(12) United States Patent
Montclare et al.

(10) Patent No.: US 9,359,408 B2
(45) Date of Patent: Jun. 7, 2016

(54) FLUORINATED PROTEIN-BASED POLYMERIC CARRIERS

(71) Applicant: New York University, New York, NY (US)

(72) Inventors: Jin Kim Montclare, New York, NY (US); Carlo Yuvienco, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/948,598

(22) Filed: Jul. 23, 2013

(65) Prior Publication Data
US 2013/0331465 A1     Dec. 12, 2013

Related U.S. Application Data

(63) Continuation-in-part of application No. 12/141,192, filed on Jun. 18, 2008.

(60) Provisional application No. 60/944,545, filed on Jun. 18, 2007.

(51) Int. Cl.
| | | |
|---|---|---|
| *C07K 14/00* | (2006.01) | |
| *A61K 47/42* | (2006.01) | |
| *A61K 9/51* | (2006.01) | |

(52) U.S. Cl.
CPC ............... *C07K 14/00* (2013.01); *A61K 9/5169* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 7,030,208 B2 * | 4/2006 | Yalpani | .......................... 528/328 |
| 2002/0164810 A1 | 11/2002 | Dukor et al. | |
| 2003/0003135 A1 | 1/2003 | Leung et al. | |
| 2004/0115180 A1 | 6/2004 | Abdelouahed | |

OTHER PUBLICATIONS

Kotze, et al. (1997) "Chitosans for enhanced delivery of therapeutic peptides across intestinal epithelia: in vitro evaluation in Caco-2 cell monolayers", International Journal of Pharmaceutics, 159: 243-53.*
Shih, et al. (2001) "The production of poly-(γ-glutamic acid) from microorganisms and its various applications", Bioresource Technology, 79(3): 207-25.*
Haghpanah, et al. (2009) "Artificial Protein Block Copolymers Blocks Comprising Two Distinct Self-Assembling Domains", ChemBioChem, 10: 2733-35.*
Nuhn et al., Secondary Structure Formation and LCST Behavior of Short Elastin-Like Peptiedes, Biomacromolecules 2008, pp. 2755-2763, vol. 9, No. 10, American Chemical Society.
Trabbic-Carlson et al., Effect of protein fusion on the transition temperature of an environmentally responsive elastin-like polypeptide: a role for surface hydrophobicity, Protein Engineering, Design & Selection 2004, p. 57-66, vol. 17, No. 1.
Cho et al., Engineered Protein Polymers, Polymer Preprints (American Chemical Society, Division of Polymer Chemistry) 47(2): 227-228 (Sep. 2006).
Guo et al., All-trans retinol, vitamin D and other hydrophobic compounds bind in the axial pore of the five-stranded coiled-coil domain of cartilage oligomeric matrix protein, EMBO Journal 17(18): 5265-5272 (1998).
Megeed et al., Genetically Engineered silk-elastinlike protein polymers for controlled drug delivery, Advanced Drug Delivery Reviews 54: 1075-1091 (2002).

\* cited by examiner

*Primary Examiner* — Robert M Kelly
(74) *Attorney, Agent, or Firm* — Hodgson Russ LLP

(57) ABSTRACT

A biologically derived polymer that facilitates the solubilization and protection of small molecules for use in drug delivery, in which the polymer is a protein polymer. A biologically derived polymer that facilitates the solubilization and protection of small molecules for use in drug delivery, incorporating fluorinated amino acids into the protein polymer for visualization and detection by $^{19}F$ NMR, $^{19}F$ MRS, and $^{19}F$ MRI.

11 Claims, 8 Drawing Sheets

FLUORINATED PROTEIN-BASED POLYMERIC CARRIERS

STATEMENT OF RELATED APPLICATIONS

The present patent application claims the benefit of pending U.S. patent application Ser. No. 12/141,192 having a filing date of 18 Jun. 2008, which claims the benefit of expired U.S. Provisional Patent Application No. 60/944,545 having a filing date of 18 Jun. 2007.

SEQUENCE LISTING

The instant application contains a Sequence Listing which has been submitted in ASCII format via EFS-Web and is hereby incorporated by reference in its entirety. Said ASCII copy, created on Aug. 22, 2013, is named 48467.055U1_SL.txt and is 26,008 bytes in size.

BACKGROUND OF THE INVENTION

1. Technical Field

The present invention is generally related to the field of biologically derived polymers for use in drug delivery and tissue engineering, and is more specifically related to biologically derived polymers that facilitate the solubilization and protection of small molecules for use in drug delivery, ranging from the delivery of common essential vitamins to complex small molecule therapeutics.

2. Prior Art

Advancements in drug delivery have often been challenged with the problem of controlled targeting. To date, passive and active targeting strategies have been operating with a shroud, hiding the journey that an active compound takes upon introduction into the living system. Common passive strategies take advantage of the enhanced permeability and retention (EPR) effect observed in sites of tumor growth. Maeda, H. The enhanced permeability and retention (EPR) effect in tumor vasculature: the key role of tumor-selective macromolecular drug targeting. Adv Enzyme Regul 41, 189-207 (2001). Other strategies rely on surgically focused triggering mechanisms such as hyperthermally controlled assembly of carrier agents, coupled to release of active compounds. Yatvin, M. B., Weinstein, J. N., Dennis, W. H. & Blumenthal, R. Design of liposomes for enhanced local release of drugs by hyperthermia. Science 202, 1290-1293 (1978). All of these strategies rely on control of delivery at the end-point site; no component of the current solutions addresses the possible path that the delivery agent and/or active compound may take en route. Thus, questions of in vivo degradation, absorption, accumulation, and metabolization of the drug still remain questions for every drug and delivery agent thereof. In addition, drug delivery, ranging from the delivery of common essential vitamins to complex small molecule therapeutics, is often stymied by issues of compound solubility and point-of-use activity.

In the field's attempt to monitor the drug delivery process, research groups have attempted to radioactively label drug delivery vehicles based on ELP sequences and monitor the in vivo environment via sampling and subsequent ex vivo measurement. Liu, W., Dreher, M. R., Chow, D. C., Zalutsky, M. R. & Chilkoti, A. Tracking the in vivo fate of recombinant polypeptides by isotopic labeling. J Control Release 114, 184-192, (2006). Similarly, epitopic labeling of drug delivery vehicles has been attempted, but observation is still an ex vivo process. Ong, S. R. et al. Epitope tagging for tracking elastin-like polypeptides. Biomaterials 27, 1930-1935, (2006). Recently, paramagnetic chemical exchange saturation transfer (PARACEST) technology has been developed to enable competitive binding experiments to be monitored non-quantitatively in vivo, Ali, M. M., Yoo, B. & Pagel, M. D. Tracking the relative in vivo pharmacokinetics of nanoparticles with PARACEST MRI. Mol Pharm 6, 1409-1416, (2009); however, this MRI technique requires the use of complexing active compounds to contrast agents containing rare heavy metals, driving the price and immunological complexity of the procedure up significantly.

Accordingly, there is a need for biologically derived polymers that facilitate the solubilization and protection of small molecules for use in drug delivery, ranging from the delivery of common essential vitamins to complex small molecule therapeutics. It is to this need and others that the present invention is directed.

BRIEF SUMMARY OF THE INVENTION

Briefly, the instant invention is a biologically derived polymer that facilitates the solubilization and protection of small molecules for use in drug delivery, ranging from the delivery of common essential vitamins to complex small molecule therapeutics. The incorporation of fluorinated amino acids into the protein polymer would potentially allow them to be imaged in vivo using magnetic resonance spectroscopy (MRS) and magnetic resonance imaging (MRI) technology enabling diagnosis. Beyond drug delivery, the instant invention also may be developed as a biomaterial scaffold for reactive tissue regeneration. The MRI-responsive fluorine in the material would allow the healing process to be monitored, quantitatively, as gradual degradation of the material is concurrent with tissue re-growth. This thereby provides biomedical engineers with a quantitative assessment for potential tissue regeneration scaffolds.

The instant invention by-passes many of these developing technologies' limitations by being completely proteinaceous in composition (aside from the stored active compound). This allows the cells or tissues to naturally degrade the delivery agent upon expenditure of its function. The tracking of the particles themselves is enabled not by metal-rich contrast agents, but rather by the naturally abundant fluorine isotope—$^{19}$F.

The biosynthesis and characterization of fluorinated protein block polymers comprised of the two self-assembling domains (SADs): elastin (E) and the coiled-coil region of cartilage oligomeric matrix proteins (C). Fluorination is achieved by residue-specific incorporation of p-fluorophenylalanine (pFF) to create pFF-EC, pFF-CE, and pFF-ECE. While pFF is incorporated herein, it is possible to incorporate other fluorinated amino acids vis residue-specific incorporation. Global fluorination results in downstream effects on the temperature-dependent secondary structure, supramolecular assembly, and bulk mechanical properties. The impact of fluorination on material properties also differs depending on the orientation of the block configurations as well as the number of domains in the fusion. This invention suggests that integration of fluorinated amino acids within protein materials can be employed to tune the material properties, especially mechanical integrity.

These features, and other features and advantages of the present invention will become more apparent to those of ordinary skill in the relevant art when the following detailed description of the preferred embodiments is read in conjunc-

BRIEF DESCRIPTION OF THE DRAWINGS

FIG. 1 illustrates three block copolymer proteins subjected to residue specific substitution of phenylalanine residues with pFF. The scheme shows the primary sequences for (a) pFF-EC (SEQ ID NO: 15), (b) pFF-CE (SEQ ID NO: 23), and (c) pFF-ECE (SEQ ID NO: 17) constructs, each containing 6, 6, and 11 phenylalanine sites, respectively, and the overall architecture of the proteins, which consist of N-terminal His6-tag (SEQ ID NO: 21) regions, elastin domains (black), and COMP (red) domains. The E (SEQ ID NO: 24) and C (SEQ ID NO: 25) domains are flanked by linker regions containing repeats of AT.

DETAILED DESCRIPTION OF PREFERRED EMBODIMENTS

Figure 1:
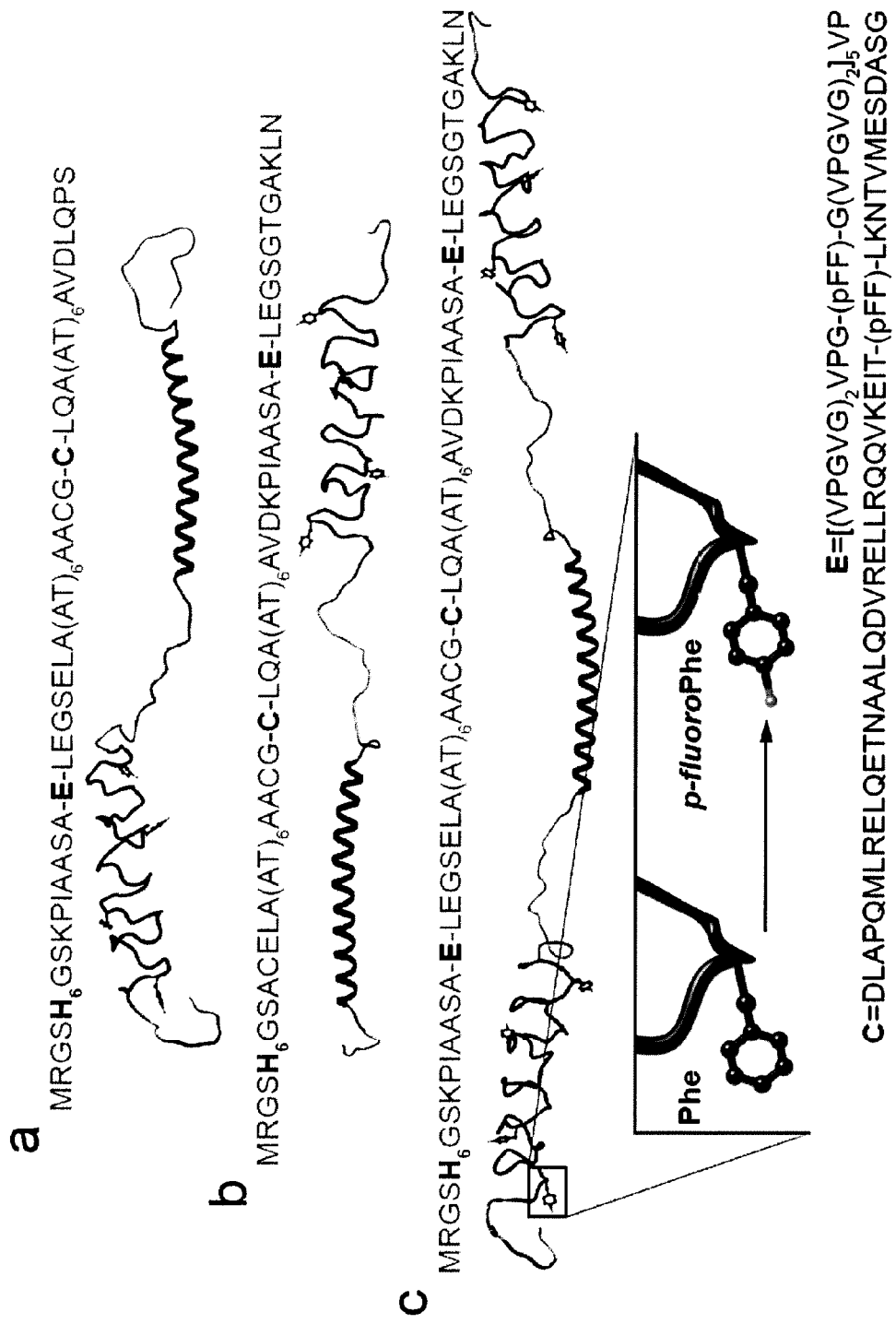

The protein domains that compose the protein homopolymer invention are 1) an elastin-like peptide (ELP) of varying repeat lengths and 2) the coiled-coil domain of cartilage oligomeric matrix protein (COMPcc). The fusion of these domains grants the invention with the ability to structurally self-assemble based on application temperature as well as the ability to bind small hydrophobic molecules. Haghpanah, J. S. et al. Artificial protein block copolymers blocks comprising two distinct self-assembling domains. Chembiochem 10, 2733-2735, (2009).

The ELP region forms microscopic structures upon incubation at elevated temperatures (e.g. 37° C.) that may be utilized for cell-seeding properties. Liu, J. C., Heilshorn, S. C. & Tirrell, D. A. Comparative cell response to artificial extracellular matrix proteins containing the RGD and CS5 cell-binding domains. Biomacromolecules 5, 497-504, (2004). Additionally, the ELP region may be used to sequester neighboring homopolymers to concentrate in a localized, thermally elevated microenvironment.

The COMP region assembles with other COMP regions to form a pentameric pore, lined with a hydrophobic interior that is 73 Å long and 2-6 Å wide. Ozbek, S., Engel, J. & Stetefeld, J. Storage function of cartilage oligomeric matrix protein: the crystal structure of the coiled-coil domain in complex with vitamin D(3). EMBO J 21, 5960-5968 (2002). The binding of small molecules within this pore structure enables the solubilization of small hydrophobic molecules in aqueous environments.

Extension of the ELP sequence by encoded repetition of the motif, defined by VPGVGVPGVGVPGFGVPGVGVPGVG (SEQ ID NO: 22), has resulted in the generation of a library of fusion proteins and the ultimate tuning of physicochemical properties of the protein fusion as a delivery carrier. Biomacromolecules 2011 12 (12), 4240-4246.

Augmenting further the various structural and delivery functions of the invention, the incorporation of fluorinated amino acids (e.g. para-fluorophenylalanine) into the protein allows for $^{19}$F NMR detection and subsequent $^{19}$F MRS and $^{19}$F MRI (3-dimensional) location of the protein fusion in solution.

The incorporation of fluorinated amino acids into the protein polymer allows them to be imaged in vivo using $^{19}$F MRS and $^{19}$F MRI technology. The MRS- and MRI-responsive fluorine in the material would allow the monitoring of the drug being delivered and the healing process to be monitored, quantitatively, as gradual degradation of the material is concurrent with tissue re-growth. This thereby provides biomedical engineers with a quantitative assessment for potential tissue regeneration scaffolds. Beyond drug delivery, the instant invention also may be developed as a biomaterial scaffold for reactive tissue regeneration.

Generally, a cloned sequence of COMPcc useful for the present invention has an N-terminal histidine tag for facile purification into a Pqe9 vector was as follows:

(SEQ ID NO: 1)
MRGSHHHHHHGSGDLAPQMLRELQETNAALQDVRELLRQQVKEITFLKNT

VMECDACGKLN

It also is possible to express in a different vector that does not necessarily bear the N-terminal histidine tag. The coiled-coil region of COMP has the following sequence:

(SEQ ID NO: 2)
GDLAPQMLRELQETNAALQDVRELLRQQVKEITFLKNTVMECDACGKLN.

In these examples, the construct can be covalently attached to fatty acids, other polymers and/or can be fused with other proteins like elastin, silk, collagen, or keratin.

Preferably, the COMPcc homopolymer (and variants thereof) as well as block polymers of COMPcc are purified using conventional methods. Illustrative COMPcc sequences and their molecular weights that are suitable for use in the present invention are provided below.

COMPcc homopolymer and variants:

(SEQ ID NO: 3)
wt:
MRGSHHHHHHGDLAPQMLRELQETNAALQDVRELLRQQVKEITFLKNTVME

CDACGKLN [6.9 KDa]

(SEQ ID NO: 4)
S:
MRGSHHHHHHGDLAPQMLRELQETNAALQDVRELLRQQVKEITFLKNTVME

SDASGKLN [6.9 KDa]

(SEQ ID NO: 5)
L37A:
MRGSHHHHHHGDLAPQMLREAQETNAALQDVRELLRQQVKEITFLKNTVME

SDASGKLN [6.9 KDa]

(SEQ ID NO: 6)
T40A:
MRGSHHHHHHGDLAPQMLRELQEANAALQDVRELLRQQVKEITFLKNTVME

SDASGKLN [6.9 KDa]

(SEQ ID NO: 7)
L44A:
MRGSHHHHHHGDLAPQMLRELQETNAAAQDVRELLRQQVKEITFLKNTVME

SDASGKLN [6.9 KDa]

(SEQ ID NO: 8)
L47A:
MRGSHHHHHHGDLAPQMLRELQETNAALQDARELLRQQVKEITFLKNTVME

SDASGKLN [6.9 KDa]

(SEQ ID NO: 9)
L51A:
MRGSHHHHHHGDLAPQMLRELQETNAALQDVRELARQQVKEITFLKNTVME

SDASGKLN [6.9 KDa]

(SEQ ID NO: 10)
Q54A:
MRGSHHHHHHGDLAPQMLRELQETNAALQDVRELLRQAVKEITFLKNTVME

SDASGKLN [6.9 KDa]

(SEQ ID NO: 11)
I58A:
MRGSHHHHHHGDLAPQMLRELQETNAALQDVRELLRQQVKEATFLKNTVME

SDASGKLN [6.9 KDa]

(SEQ ID NO: 12)
L61A:
MRGSHHHHHHGDLAPQMLRELQETNAALQDVRELLRQQVKEITFAKNTVME

SDASGKLN [6.9 KDa]

(SEQ ID NO 13)
V65A:
MRGSHHHHHHGDLAPQMLRELQETNAALQDVRELLRQQVKEITFLKNTAME

SDASGKLN [6.9 KDa]

(SEQ ID NO: 14)
S65A:
MRGSHHHHHHGDLAPQMLRELQETNAALQDVRELLRQQVKEITFLKNTVME

ADASGKLN [6.9 KDa]

COMPcc block polymers:

(SEQ ID NO: 15)
Elastin-COMPcc--MRGSHHHHHG S K P I A A S A V P G V G V P G V G V P G F G

V P G V G V P G V G V P G V G V P G V G V P G F G V P G V G V P G V G

V P G V G V P G V G V P G F G V P G V G V P G V G V P G V G V P G V G

V P G F G V P G V G V P G V G V P G V G V P G V G V P G F G V P G V G

V P G V G V P L E G S E L A A T A T A T A T A T A A C G D L A P Q

Met L R E L Q E T N A A L Q D V R E L L R Q Q V K E I T F L K N T V Met

E S D A S G L Q A A T A T A T A T A T A V D L Q P S [22.38 KDa]

(SEQ ID NO: 16)
COMPcc-Elastin--MRGSHHHHHG S A G E L A A T A T A T A T A T A A C G D L A P Q Met L R E L Q E T N A A L Q D V R E L L R Q Q V K E I T F L K N T V Met E S D A S G L Q A A T A T A T A T A T A V D K P I A A S A

V P G V G V P G V G V P G F G V P G V G V P G V G V P G V G V P G V G

-continued
V P G F G V P G V G V P G V G V P G V G V P G V G V P G F G V P G V G

V P G V G V P G V G V P G V G V P G F V G P G V G V P G V G V P G V G

V P G V G V P G F G V P G V G V P G V G V P L E G S G T G A K L [22.65 KDa]

(SEQ ID NO: 17)

Eastin-COMPcc-Elastin--MRGSHHHHHHG S K P I A A S A V P G V G V P G V G V P

G F G V P G V G V P G V G V P G V G V P G V G V P G F G V P G V G V P G V G

V P G V G V P G V G V P G F G V P G V G V P G V G V P G V G V P G V G V P G

F G V P G V G V P G V G V P G V G V P G V G V P G F G V P G V G V P G V G V

P L E G S E L A A T A T A T A T A T A T A A C G D L A P Q Met L R E L Q E T

N A A L Q D V R E L L R Q Q V K E I T F L K N T V Met E S D A S G L Q A A T

A T A T A T A T A T A V D K P I A A S A V P G V G V P G V G V P G F G V P G

V G V P G V G V P G V G V P G V G V P G F G V P G V G V P G V G V P G V G V

P G V G V P G F G V P G V G V P G V G V P G V G V P G V G V P G F G V P G V

G V P G V G V P G V G V P G V G V P G F G V P G V G V P G V G V P L E G S

T G A K L N [34.17 KDa]

The current sequences in which successful incorporation of non-natural amino acids has been observed are as follows. These sequence designations include a library of proteins for which a variable length ELP region is encoded and repeated up to n times.

EC:
(SEQ ID NO: 18)
MRGSHHHHHHGSKPIAASA(VPGVGVPGVGVPGFGVPGVGVPGVG)$_n$VPL

EGSELAATATATATATATAACGDLAPQMLRELQETNAALQDVRELLRQQV

KEITFLKNTVMESDASGLQAATATATATATATATAVDLQPS

CE:
(SEQ ID NO: 19)
MRGSHHHHHHGSACELAATATATATATATATAACGDLAPQMLRELQETNAAL

QDVRELLRQQVKEITFLKNTVMESDASGLQAATATATATATATATAVDKPIA

ASA(VPGVGVPGVGVPGFGVPGVGVPGVG)$_n$VPLEGSGTGAKL

ECE:
(SEQ ID NO: 20)
MRGSHHHHHHGSKPIAASA(VPGVGVPGVGVPGFGVPGVGVPGVG)$_n$VPL

EGSELAATATATATATATAACGDLAPQMLRELQETNAALQDVRELLRQQV

KEITFLKNTVMESDASGLQAATATATATATATATAVDKPIAASA(VPGVGVP

GVGVPGFGVPGVGVPGVG)$_n$VPLEGSGTGAKL

The $^{19}$F NMR signal as well as the $^{19}$F solid-state NMR signal is obtainable for the fluorinated proteins of the present invention.

This invention benefits various fields such as regenerative medicine, pharmaceuticals, and nutritional supplementation, allowing researchers to observe in vivo delivery dynamics of their molecules of interest.

Genetically engineered proteins have made a significant impact in biomaterials research, enabling the fabrication of polymers with monodisperse molecular weights, a diverse set of side chain functionality, and well-defined secondary structure elements. Protein materials with defined physicochemical properties and function have been achieved, however, the chemical functional group diversity is limited by the natural amino acids. Recent advances in unnatural amino acid incorporation enable the integration of chemical diversity into such proteins, further expanding the level of control of materials properties. Fluorinated amino acids (Faa's) have been employed in protein design to imbue resistance to chemical or heat denaturation endoprotease activity, as well as enable self-sorting of dimeric peptides and proteins. Baker, P. J., et al., ChemBioChem. 2011, 12, 1845; Bilgiçer, B., et al., Am. Chem. Soc. 2001, 123, 11815. Residue-specific incorporation of Faa's into protein materials can impart stereo-electronic as well as steric effects that can influence stability. Biffinger, J. C., et al., ChemBioChem 2004, 5, 622; Kim, W., et al., Chem., Int. Ed. 2006, 45, 8141; Lee, K.-H., et al., Biochemistry 2004, 43, 16277. Whereas previous groups have investigated the effects of Faa's on turn residues of structural proteins, herein we describe the effects of fluorination on the overall assemblies from the nano- to macroscale.

Recently, we have demonstrated that protein block polymers consisting of two self-assembling domains (SADs), derived from elastin (E) and the coiled-coil domain of COMP (C), in the configurations EC, CE, and ECE, exhibit distinct modes of assembly. Baker, P. J, et al., In Polymer Biocatalysis and Biomaterials II; Cheng, H. N., et al., eds., American Chemical Society: Washington, D.C., 2008, Vol. 999, p 37; Gunasekar, S. K., et al, Biochemistry 2009, 48, 8559; Gunasekar, S. K., et al, Polym. Adv. Technol. 2008, 19, 454; Guo, Y., et al., EMBO J. 1998, 17, 5265; Haghpanah, J. S., et al., ChemBioChem 2009, 10, 2733; Haghpanah, J. S., et al., Mol. BioSyst. 2010, 6, 1662. The SAD arrangements and quantity within a single protein polymer chain essentially impacts the structure, supramolecular assembly, and mechanical properties. The SADs were designed to embody the hybrid functionality of E-based thermoresponsive assembly and the binding capacity of the C domain, with the original intention for applications in small molecule encapsulation and delivery. Herein we explore the effects of incorporating parafluorophenylalanine (pFF) into the protein block polymer sequences to produce pFF-EC, pFF-CE, and pFF-ECE in an attempt to modulate their self-assembly processes on a secondary structural basis as well as a bulk macroscopic basis (FIG. 1). We observe that incorporation of fluorinated amino acids is able not only to modulate the transition temperature ($T_t$) of the proteins, but also the cooperativity of these transitions. Opportunities to modulate physicochemical behavior, such as this, become increasingly important for protein- and peptide-based materials systems. Incorporation of fluorinated amino acids is particularly relevant to systems known to assemble via hydrophobic interactions such as elastin, silk elastin, and oligopeptide assemblies. While attempts to tune physicochemical behavior have included modification to sequence patterns and length, as well as solvent conditions and cross-linking via chemical modification, we demonstrate that this can be achieved through modification of the basis set of building blocks. Urry, D. W., et al., Biopolymers 1985, 24, 2345; Meyer, D. E., et al., Biomacromolecules 2004, 5, 846; Rammensee, S., et al., Appl. Phys. A: Mater. Sci. Process. 2006, 82, 261.

Biosynthesis. PQE30/EC, PQE30/CE, and PQE30/ECE, previously constructed, were each transformed into *E. coli* strain AF-IQ auxotrophic cells. Cell growth and proteins was accomplished via previously established methods. Voloshchuk, N., et al., Bioorg. Med. Chem. Lett. 2009, 19, 5449. In brief, cells were cultured in M9 supplemented media, bearing 20 amino acids, ampicillin (200 μg mL$^{-1}$), and chloramphenicol (35 μg mL$^{-1}$), for 6 h at 37° C. and subsequently pelleted and subjected to an extensive washing step with ice-cold 0.9% NaCl that was repeated two times. The washed culture pellet was resuspended in fresh M9 supplemented media, containing 19 amino acids, ampicillin (200 μg mL$^{-1}$), and chloramphenicol (35 μg mL$^{-1}$), and grown for 30 min at 37° C., in accordance to Yoshikawa et al., Macromolecules 1994, 27, 5471, to fully deplete residual phenylalanine. After 30 min, protein expression was induced via the addition of isopropyl β-D-1-thiogalactopyranoside (IPTG, 100 μg mL$^{-1}$) in the absence or presence of phenylalanine (Phe, 1 mg mL$^{-1}$) or pFF (91.59 mg mL$^{-1}$). Cells were harvested and osmotically shocked prior to immobilized metal affinity chromatography (IMAC) column purification under denaturing conditions (50 mM phosphate buffer, 6 M urea). Clarified whole cell lysate was applied to a 5 mL HiTrap IMAC FastFlow column (GE Life Sciences), charged with CoCl$_2$, using an ÄKTA purifier system (GE Life Sciences). The protein was eluted across 5 mL of 48 mM imidazole and 15 mL of 1 M imidazole. Purified proteins were dialyzed extensively against water via a 3500 MWCO membrane (SnakeSkin Dialysis Tubing, Pierce) and subsequently freeze-dried prior to use.

Incorporation Analysis. Incorporation levels of pFF were assessed via matrix-assisted laser desorption ionization, time-of-flight mass spectrometry analysis on an Omniflex spectrometer (Bruker Daltonics) of chymotrypsin digests of the individual proteins. Lyophilized protein samples (50-100 μg) were resuspended in 100 mM Tris-HCl and 10 mM CaCl$_2$ (pH 8.0) to a final concentration of 1.25 μg μL$^{-1}$. Sequencing grade chymotrypsin (Promega) was added to the mixtures (2% w/w). Enzymatic digestion was carried out at 25° C. for 20 h and quenched with 1% TFA. Sample mixtures were mixed with saturated solutions of α-cyano-4-hydroxycinnamic acid in 1% TFA/acetonitrile (2:1) in a 1:1 ratio. Samples were spotted onto a 7×7 OmniFlex MALDI target (Bruker Daltonics) and allowed to dry under vacuum. The intensities of peaks, which were assigned to peptide digest fragments, were compared to obtain relative incorporation levels. In addition, amino acid analysis (AAA) was performed on the same proteins and analyzed. Incorporation levels of pFF were calculated based on the measurements of normalized Phe levels in the samples.

Circular Dichroism. Circular dichroism (CD) spectroscopy was employed to assess the secondary structure of the proteins prepared to 4 μM in 10 mM phosphate buffer, pH 8.0. CD spectra were collected on a J-815 CD spectrometer (Jasco) equipped with a PTC-423S single position Peltier temperature control system. Wavelength scans were performed at constant temperatures as the samples were heated from 4 to 65° C., at a heating rate of 1° C./min. Operation and analysis parameters were adapted from existing procedures, such as in Haghpanah, J. S., et al, ChemBioChem 2009, 10, 2733. Estimation of secondary structure was performed using the CDSSTR method, Johnson, W. C., Proteins 1999, 35, 307, as distributed by DICHROWEB (Birkbeck College of the University of London), Whitmore, L., et al., Biopolymers 2008, 89, 392. The method was applied to the SDP48 protein reference set.

UV/Vis Spectroscopy. UV/vis spectroscopy was performed on a Cary 100 UV/vis spectrometer (Agilent) to determine the inverse temperature transition ($T_t$) of 4 μM protein in 10 mM phosphate buffer, pH 8.0. The absorbance at 350 nm was measured as each protein sample was heated from 10 to 65° C., at a heating rate of 0.5° C./min.

Microrheology. To assess the mechanical properties of all proteins, microrheology was performed using an inverted Leica DM-138 IRB microscope with a 20× objective lens at 22 and 42° C., maintained by a Lincum temperature-controlled cell. In brief, lyophilized proteins were dissolved in deionized water at 4° C. to two concentrations, 1.25 mg mL$^{-1}$ and 2.5 mg mL$^{-1}$. A total of 2 μL of 2 wt % fluorescent-amidated polystyrene beads (1.0 μm) was added to 10 μL of protein solution. Deionized water, 2 wt % beads, was measured as a control. Brownian motion of the beads was observed by Peltier-cooled video camera (QiCam) and digitally recorded. Mean square displacement (MSD) measurements of the beads were determined by IDL software (Research Systems, Inc.). Using the comprehensive Stokes-Einstein equation, the elastic modulus (G') and viscous modulus (G") were determined as a function of angular frequency (ω).

Figure 2:
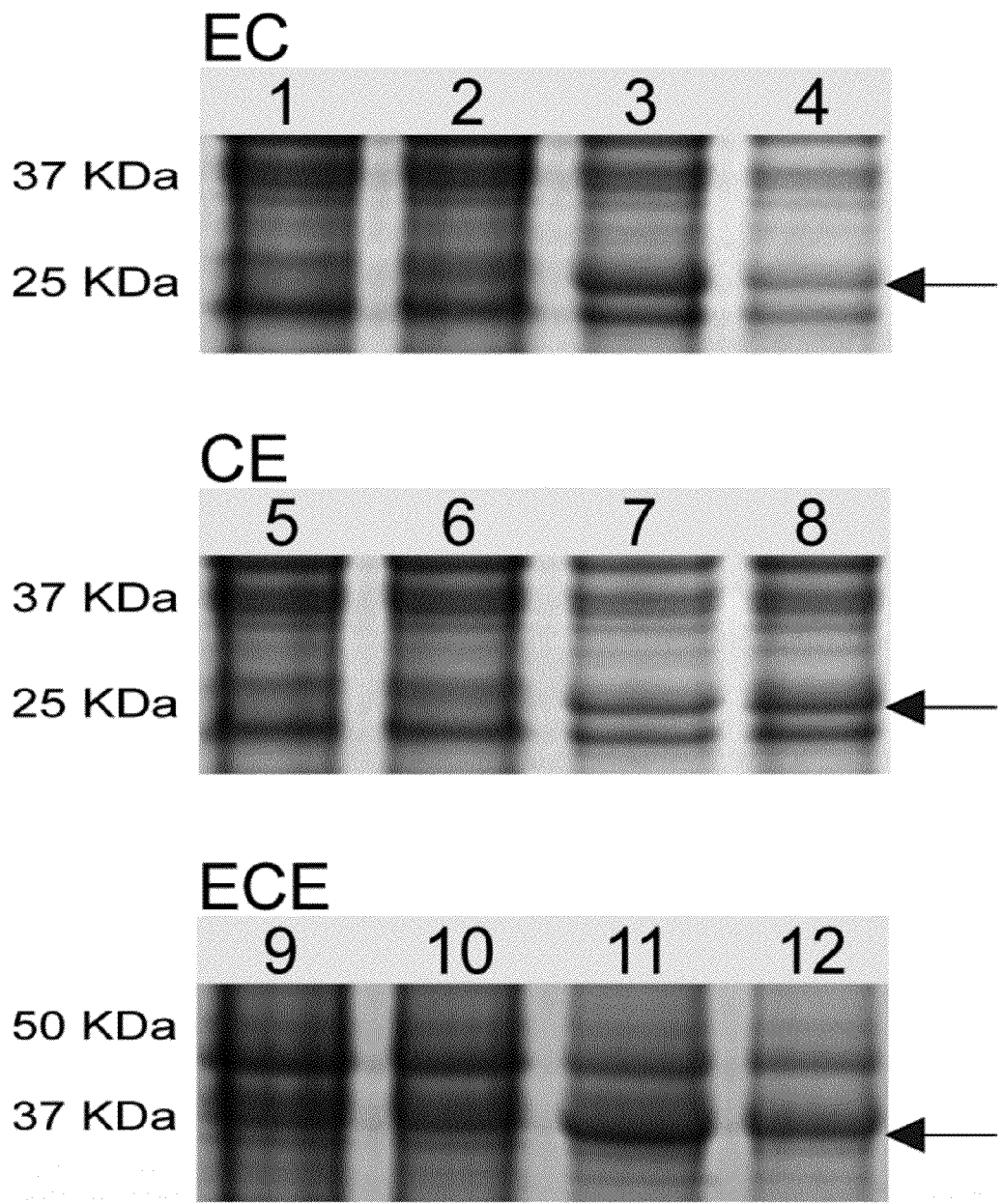
FIG. 2 illustrates confirmation of pFF-EC, pFF-CE, and pFF-ECE proteins. SDS-PAGE of whole cell lysate samples (normalized to OD600=1.0) in the absence and presence of phenylalanine (Phe) and pFF. Lanes 1, 5, and 9: preinduction lysate; 2, 6, and 10: −Phe/−pFF postinduction lysate; 3, 7, and 11: +Phe/−pFF postinduction lysate; 4, 8, and 12: −Phe/+pFF postinduction lysate. Arrows indicate protein overexpression band. The absence of the overexpression bands in lanes 1, 2, 5, 6, 9, and 10 indicates that the expression methodology does not suffer from "leaky" expression of protein, which would result in the significant contamination of F in the purified protein. Further, the comparable intensity of paired bands in lanes 3, 4, 7, 8, 11, and 12 suggests that the expression method is able to readily support the presence and incorporation of pFF in the system.

Biosynthesis of Fluorinated Block Polymers. Residue-specific incorporation of pFF was accomplished using a phenylalanine (Phe) auxotrophic *E. coli* strain AF-IQ. Expression of proteins took place in M9 minimal media, supplemented with 19 amino acids in the presence or absence of Phe and pFF (FIG. 2). In the presence of Phe or pFF, a distinct band was observed at 25 kDa for the diblocks and 37 kDa for the triblock, confirming the production of protein polymers. Protein yields from expression and purification methods were quantified to be 4.7 mg/L. To determine the levels of pFF incorporation, proteins were subjected to chymotrypsin digestion and further analyzed via MALDI-MS and AAA (FIG. 2). The discrepancy between AAA and MALDI-MS estimations for incorporation, 6-11%, are slightly higher than that observed previously for the incorporation of pFF into tGCN5, but on the same order of magnitude. Voloshchuk, N., et al. Bioorg. Med. Chem. Lett. 2009, 19, 5449. The process of residue-specific incorporation operates stochastically so as to yield fusion molecules of either 4 or 5 residues (of the total 5) in the E domain with substituted pFF residues.

Figure 3:
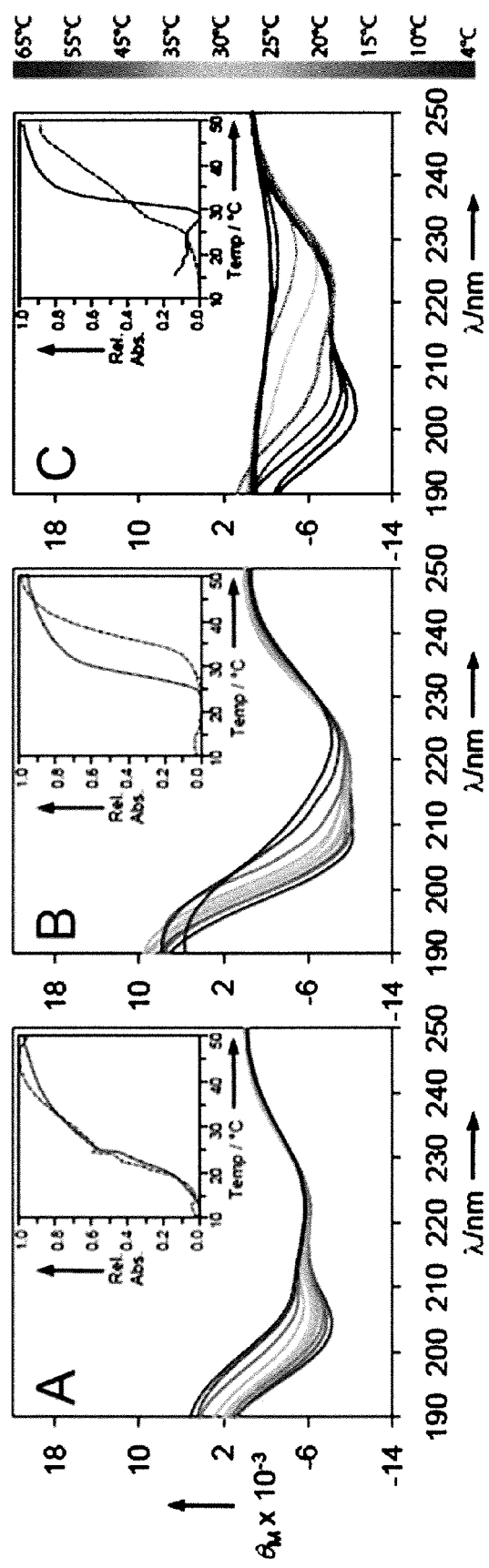
FIG. 3 illustrates CD wavelength spectra collected as a function of temperature for (A) pFF-EC, (B) pFF-CE, and (C) pFF-ECE, indicating the secondary structural changes that accompany the thermoresponsiveness of the proteins; insets show OD350 as temperature increases, indicating the inverse transform temperature ($T_t$) for pFF proteins (solid lines) and wt counterparts (dashed lines), from which are interpreted the bulk meso-/macroscale assembly that occurs with the addition of heat. For both experiments, samples were prepared to 4 μM in phosphate buffer initially at 4° C., establishing congruent preparation protocols.

Secondary Structure Analysis. To assess the impact of fluorination on secondary structure, circular dichroism (CD) spectroscopy was employed to obtain wavelength scans as a function of temperature for all fluorinated proteins. pFF-EC was randomly structured at low temperatures, transitioning to an α+β-rich conformation at higher temperatures (FIG. 3). By contrast, pFF-CE revealed a more structured α+β conformation at temperatures less than 30° C. Upon heating from 30 to 65° C., pFF-CE adopted a predominantly β-rich structure indicated by a single minimum present above 220 nm. pFF-ECE revealed a highly cooperative transition from a randomly structured protein to a β-rich protein (indicated by the single minimum at 30° C.), eventually losing all evidence of structure. The secondary structures depend on the orientation of the block segments and the number block segments, consistent with the behavior of the wild-type (wt) proteins. While both fluorinated diblocks appeared to exhibit minimal deviation in structure relative to their wt counterparts, pFF-ECE only resembled its wt analogue at lower temperatures and conformed to a β-rich structure at higher temperatures. The wt ECE spectra exhibited an isodichroic point, indicative of a two-state transition, a feature clearly absent among the pFF-ECE spectra.

Temperature-Dependent Supramolecular Assembly. The effect of temperature on the supramolecular assembly of the proteins was examined via absorption at 350 nm. The inverse temperature transition ($T_t$) was determined via temperature-dependent absorption (FIG. 3, insets). The $T_t$ values for all fluorinated block polymers were different, affirming the significance of block orientation and number. The $T_t$ of pFF-EC was determined to be 25° C., while pFF-CE and pFF-ECE exhibited a $T_t$ at 28 and 32° C., respectively. In comparison to the wt proteins, fluorination appeared to depress the $T_t$ of CE protein from 36 to 28° C. While fluorination did not affect the $T_t$ of EC or ECE proteins, an enhanced cooperativity was observed in the transition for ECE.

Figure 4:
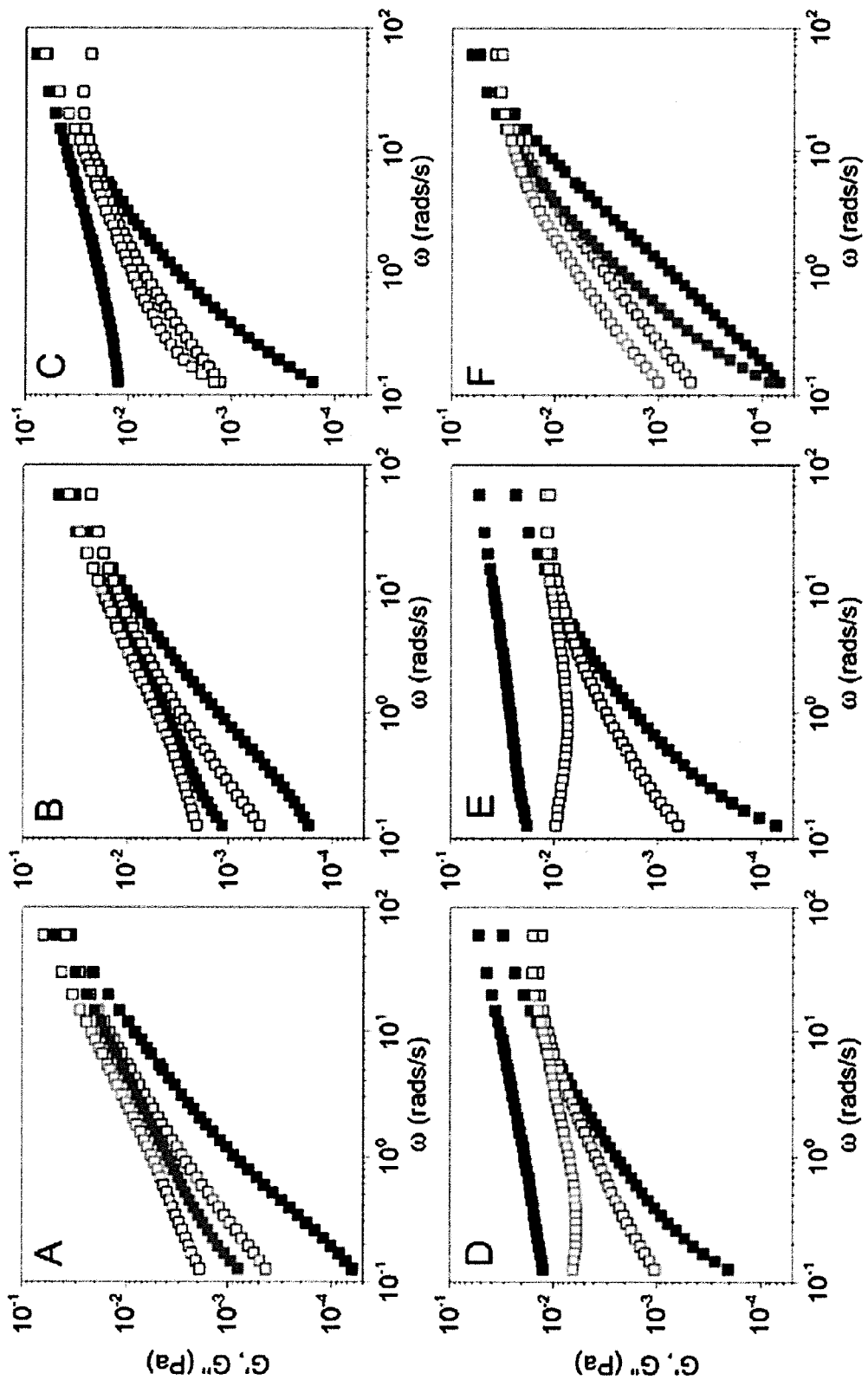
FIG. 4 illustrates microrheological data, derived from tracked particle movements within protein solutions, comparing the predominance of either viscous, elastic, or viscoelastic characters observed for (A, D) pFF-EC, (B, E) pFF-CE, and (C, F) pFF-ECE, at 1.25 mg mL$^{-1}$ (A-C) and 2.5 mg mL$^{-1}$ (D-F). Charts display storage (filled markers) and loss (empty markers) moduli at 22° C. (black) and 42° C. (red). The crossover of moduli at 22° C. in set (A, D) indicates viscoelastic behavior for pFF-EC, distinct from wt-EC. The dominant elastic modulus at 42° C. in panel E indicates elastic behavior for pFF-CE, which exists as a viscoelastic material in the wt analogue. Significant to panel C is both the apparent shift in critical concentration to induce a thermoresponsive change in mechanical properties, as well as the indication of elastic behavior vis-à-vis the exclusive viscoelastic behavior of the weight analogue.
Figure 5:
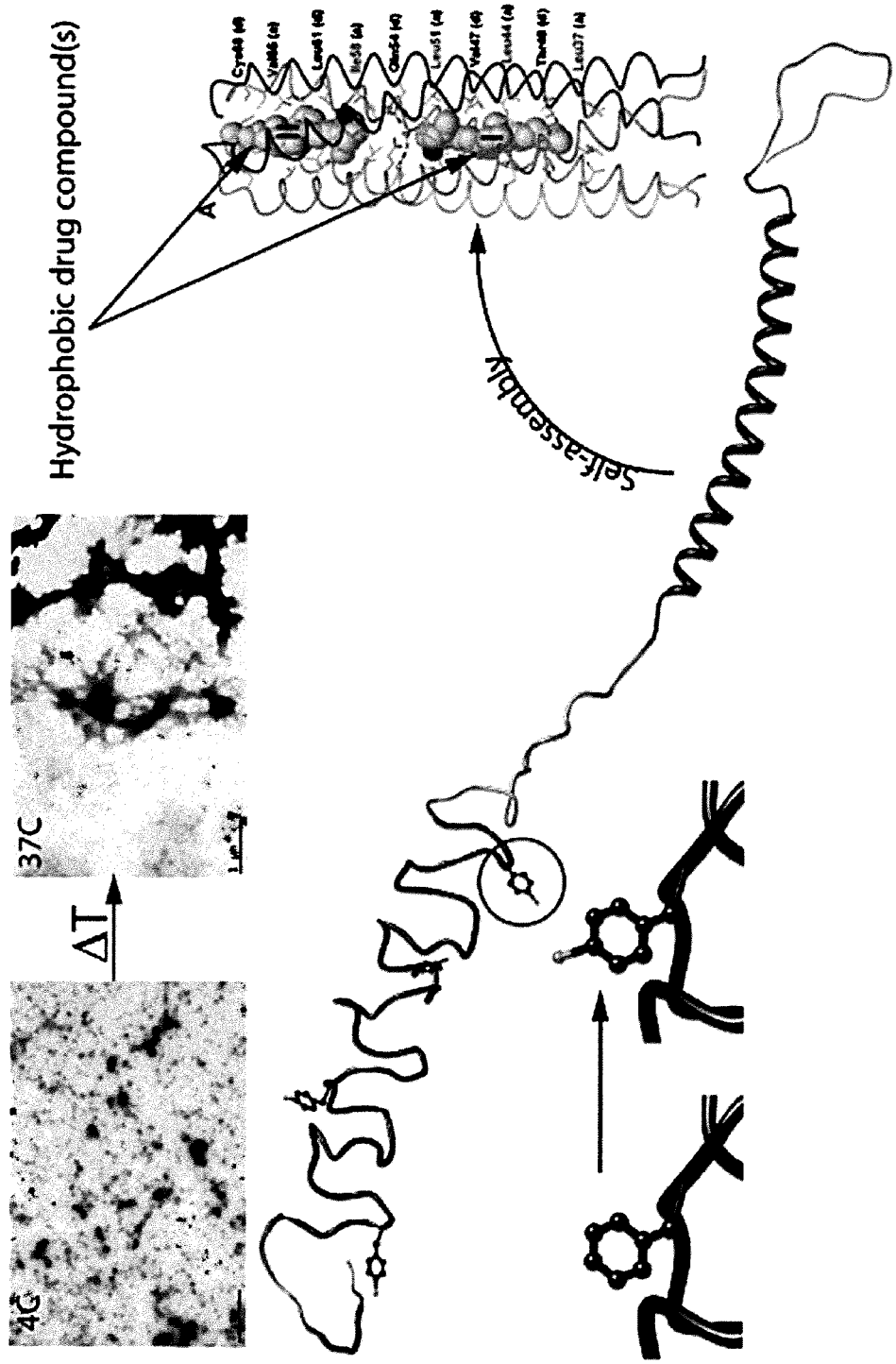
FIG. 5 illustrates the pFF-EC and formation of nanoparticles via TEM. These nanoparticles at elevated temperature (4-37° C.) demonstrate aggregation due to the E (elastin) domain. The C (COMPcc) domain is able to bind small molecules in the hydrophobic pore.
Figure 6:
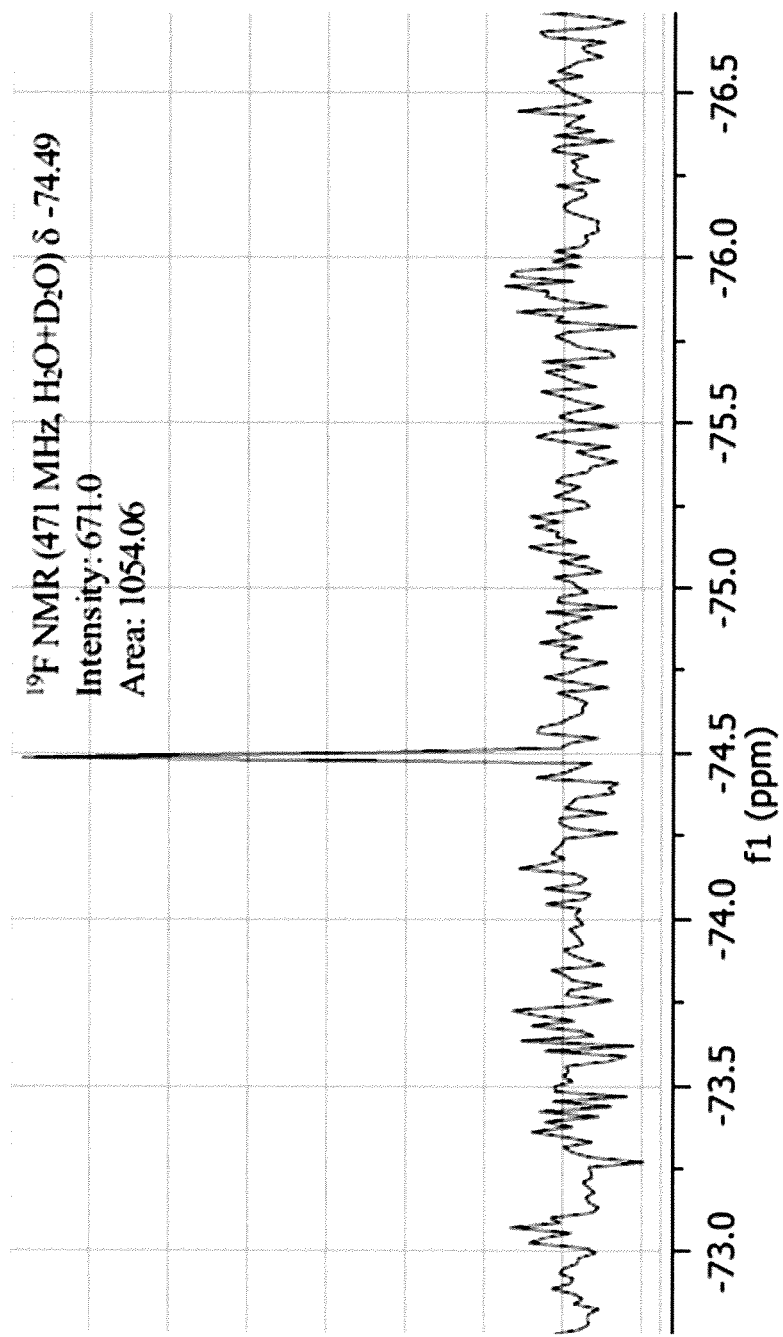
FIG. 6 illustrates a $^{19}$F NMR scan of pFF-EC supernatant after 48 hours of incubation with chymotrypsin.
Figure 7A:
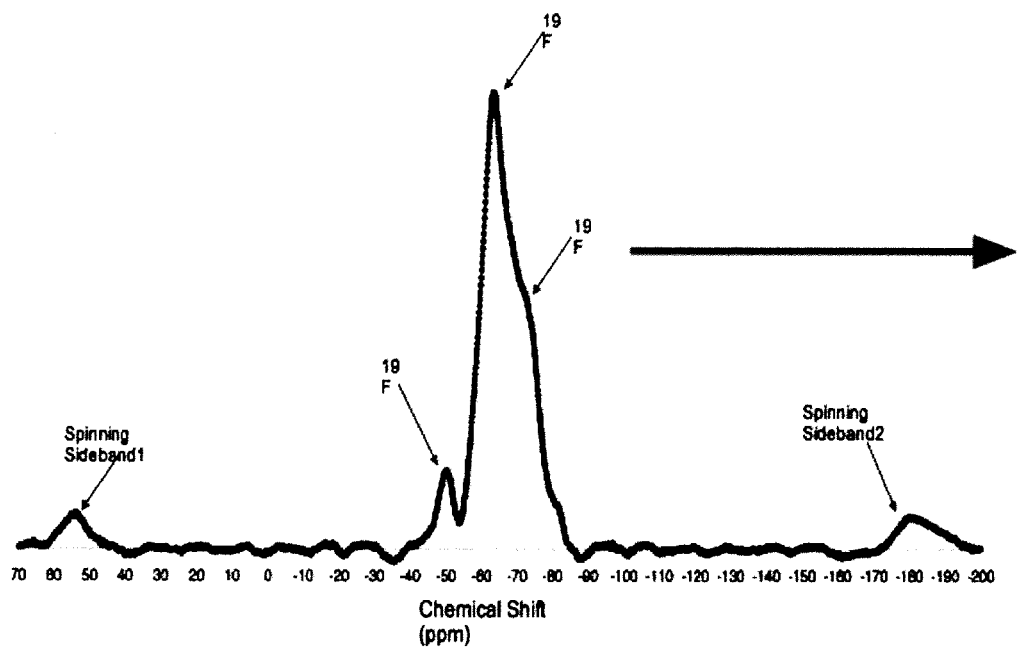
FIG. 7A illustrates 1D $^{19}$F solid-state NMR spectrum of lyophilized pFF-EC at a magic angle spinning (MAS) frequency of 33 kHz at room temperature referenced to TFA. Data suggests at least 3 distinct sites of fluorinated amino acid incorporation.
Figure 7B:
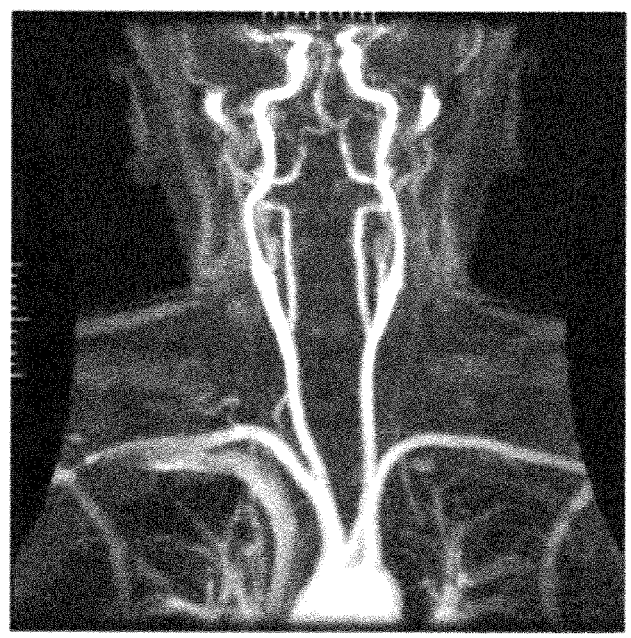
FIG. 7B illustrates corresponding solution-state NMR spectrum of pFF-EC prepared to 10 μM in 10 mM phosphate buffer, pH 8.0.
Figure 8:
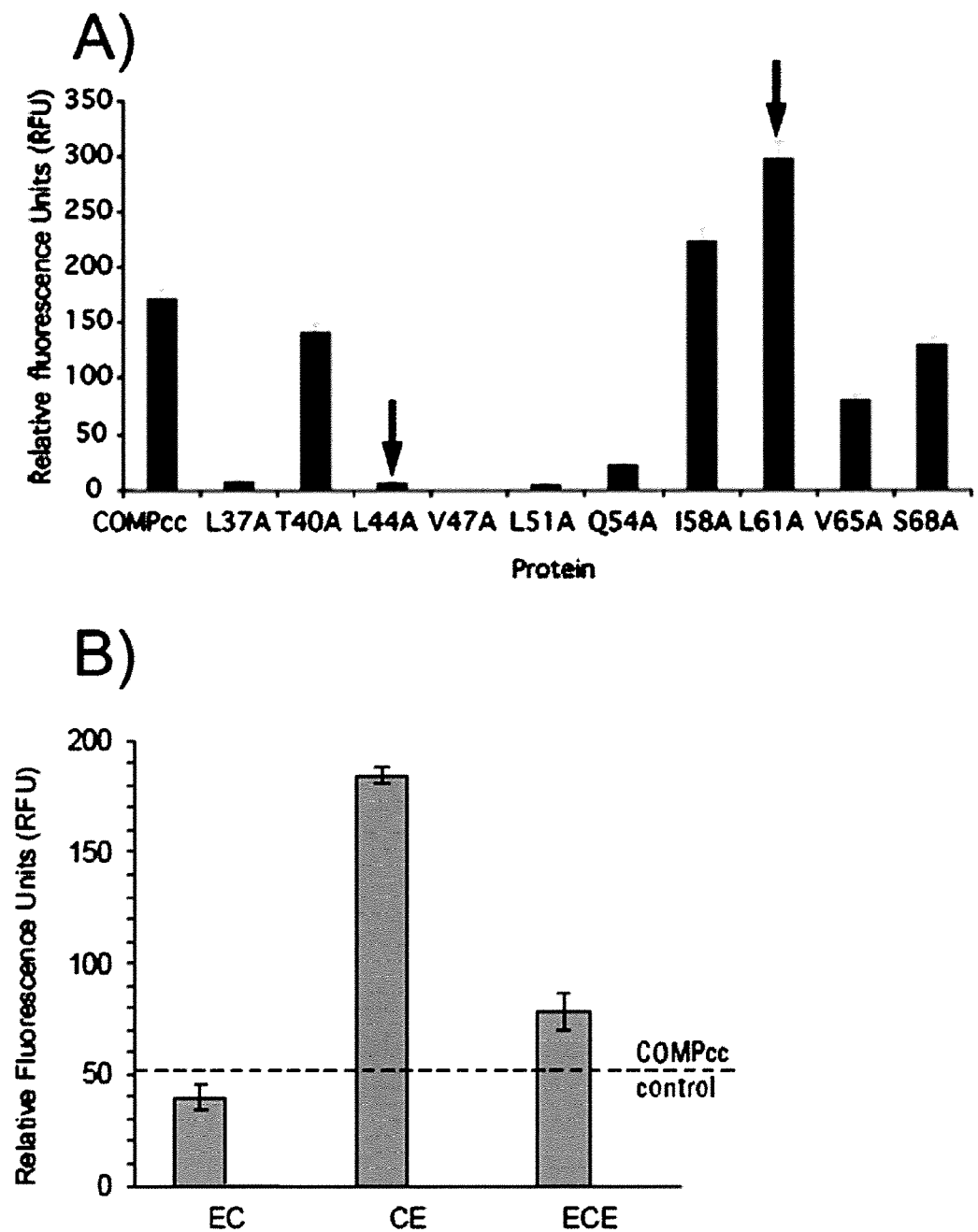
FIG. 8 illustrates binding of all-trans retinol (ATR) to (FIG. 8A) protein carrier constituent, COMP (with several single point mutations); arrows represent variants with poor and enhanced binding, respectively), and (FIG. 8B) protein carriers, as measured by ATR's inherent fluorescence triggered upon binding to proteins.

Mechanical Properties. Bulk rheological properties of the protein polymers were evaluated by microrheology (FIG. 4). Various concentrations were also prepared in an effort to identify concentration-dependent assembly of the proteins and percolation of elastic network formation (FIG. 4). Previous work by other groups demonstrated the concentration dependence of elastin-like peptide self-assembly, such as Yamaoka, T., et al, Biomacromolecules 2003, 4, 1680 and Meyer, D. E., et al., Biomacromolecules 2004, 5, 846. Indeed, wt-EC was predominantly viscous at concentrations below 2.5 mg mL$^{-1}$ and transitioned to an elastic network, as the concentration was prepared to 10 mg mL$^{-1}$. This behavior, however, was not observed for the wt-CE and wt-ECE as they existed as predominantly viscous or viscoelastic solutions up to 10 mg mL$^{-1}$, respectively.

Upon fluorination, more depressed concentration-dependent percolation points for the protein polymers were observed. While wt-EC was predominantly viscous at 1.25 mg mL$^{-1}$, pFF-EC was viscoelastic at 22° C. at the same concentration and both demonstrating more elastic character at 42° C. at 2.5 mg mL$^{-1}$ (FIG. 4A). Both the wt-CE and pFF-CE exhibited viscous/viscoelastic character at 1.25 and 2.5 mg mL$^{-1}$ at 22° C., however, at 2.5 mg mL$^{-1}$ and 42° C., pFF-CE demonstrated a dominant elastic modulus compared to the viscoelastic character of the wt-CE (FIG. 4B, E). Two types of modifications to the rheological behavior are observed from EC and CE sets of constructs. For pFF-EC, a transition shift in the required concentration to yield viscoelastic behavior is demonstrated, whereas for pFF-CE, a rheological shift to elastic behavior was observed, which was not obtainable, even at concentrations up to 10 mg mL$^{-1}$ for wt-CE.

Similar to both diblocks, pFF-ECE underwent a transition and rheological shift. pFF-ECE demonstrated a transition shift from viscous to viscoelastic fluid at 1.25 mg mL$^{-1}$ (FIG. 4C). Most significantly, pFF-ECE at 1.25 mg mL$^{-1}$ exhibited elastic network formation at 42° C., while the wt-ECE was completely viscous under the same concentration and temperature (FIG. 4C).

The suppression of elastic behavior at 42° C. for the 2.5 mg mL$^{-1}$ preparation compared to the 1.25 mg mL$^{-1}$ preparation is similar to the gel formation of fibrin clotting networks, which form "fine" transparent networks that demonstrate more elastic behavior compared to that of "coarse" opaque networks. Janmey, P. A., et al., Rheol. 1983, 27, 135; Nelb, G. W., et al., Biophys. Chem. 1976, 5, 377; Clark, A. H., et al., Biopolymers: Advances in Polymer Science, Springer: New York, 1987; p 57. In general, the incorporation of pFF facilitated percolation when compared to their wt counterparts. Moreover, fluorination yielded robust elastic network formation for all three protein polymers at elevated temperatures.

While the secondary structure appears conserved with respect to the diblock variants, the supramolecular behavior appears to have been altered, suggesting that even modest effects to the intermolecular interactions can dramatically affect the self-assembly of macromolecules. The change in conformation that accompanies the sample heating corresponds to the self-assembly that is taking place. For all three protein fluoropolymers, the supramolecular assemblies as determined by light scattering are dictated by the transitions from either unstructured to structured as in the case of pFF-EC and pFF-ECE or from α+β-rich to β-rich conformation, as demonstrated by pFF-CE. As the proteins assume more β-conformation due to the elastin composition within the constructs, they undergo self-assembly into particle aggregates. Indeed, such correlations between CD spectrograms and turbidimetry profiles have been developed by previous groups studying elastin-like peptides; the differential light scattering of polarized light effectively converts a CD signature to a damped optical rotatory dispersion curve.

Although fluorination does not affect the secondary structure or $T_t$ of pFF-EC, there is an effect on the $T_t$ of pFF-CE even though the temperature-dependent conformation is conserved. The downward shift in the $T_t$ of pFF-CE can, thus, be attributed to the promotion of supramolecular assemblies upon heating, suggested by microrheology, as opposed to secondary conformational changes. In the case of pFF-ECE, the secondary structural change correlates with the more cooperative transition and bulk mechanical response at lower concentration. We posit that the pronounced effects on supramolecular assembly upon fluorinating CE and ECE are due to a synergistic enhancement of the effect of pFF on the hydrophobic collapse of the E domain. Distinct to the CE and ECE is the dominant β-content as heat is added to the system, in contrast to the EC protein. The overall results suggest that the hydrophobic collapse and subsequent β-turn formation of the E domain is occurring and dominating the compound structure of the block proteins. As the dominant structure for the protein, the pFF residues, which are biased toward the E domain, tend to effect overall changes in the self-assembly process, observed via light scattering and microrheology. This aspect of a block system is especially significant when designing block polymer architectures that undergo biased modification such that the resultant effects may depend on the dominating structure of the overall polymer, a similar example of which was recently documented for allosteric actuation of calmodulin-elastin fusions by Kim and Chilkoti, J. Am. Chem. Soc. 2008, 130, 17867.

Fluorination alters the mechanical behavior of all the polymers with respect to either concentration or temperature responsiveness. Specifically, the results demonstrated more elastic character upon incorporation of pFF in all constructs. The data suggests that fluorination promotes supramolecular association facilitating percolation and elastic network formation. Indeed fluorination of synthetic polymers has been shown to modulate supramolecular assemblies, confirming our results with proteins polymers. Percec, V., et al., Chem., Int. Ed. 2005, 44, 4739; Krafft, M.-P., et al., Chem., Int. Ed. 1993, 32, 741; Krafft, M.-P., et al., Chem., Int. Ed. 1994, 33, 1100; Krafft, M.-P., Adv. Drug Delivery Rev. 2001, 47, 209. While the mechanical properties of the current system, particularly the magnitude of the elastic and viscous moduli, are orders of magnitude less than hydrogel systems commonly seen in biomedical applications, other systems are often characterized at higher concentrations and undergo chemical cross-linking. In fact, the elastic moduli of the constructs presented above are on the same order of magnitude ($10^{-2}$-$10^{-1}$ Pa across $10^1$-$10^2$ rad/s) as poly(L-lysine HBr)-block-(L-leucine) polymers developed and characterized by Pine et al., Macromolecules 2004, 37, 3943, and β-hairpin peptides by Pochan et al., Macromolecules 2008, 41, 5763. We further posit that cross-linking strategies could be applied to our current system to positively offset the viscoelastic moduli by orders of magnitude similar to the effects reported by Bausch et al. for recombinantly produced spider silk in Appl. Phys. A: Mater. Sci. Process. 2006, 82, 261.

While there have been numerous studies of the effects of Faa's on altering the stability and structure of proteins, both de novo and natural, the present invention demonstrates that integration of Faa's can also modify bulk material properties relevant to both the thermoresponsive behavior of E-based fusions and rheological properties of soft gel materials for biomedical applications. Indeed, the most significant and applicable alterations to the constructs upon fluorination are manifested in the enabling of unrealized rheological regimes, as in the case of pFF-CE and pFF-ECE (FIGS. 4C and E, respectively), and in the shifting of critical concentrations, as in the case of pFF-EC and pFF-ECE (FIGS. 4A and E, respectively). Furthermore, these properties of pFF-ECE are also accompanied by a more cooperative transition, making it more sensitive for applications in temperature-actuated targeting and delivery, an established application of elastin-based protein polymers. Modifications to the transition window have been effected in the past by changes in protein concentration and block orientation.

In the realm of synthetic chemistry, there has been a long standing interest in the physicochemical properties of fluorinated polymers. Self-assembly into higher-order structures has gained particular focus, in the cases of semifluorinated dendritic Janus particles and fluorinated amphiphiles, which affect assemblies on the supramolecular scale in very different ways, and despite the early successes in the incorporation of Faa's into protein polymers, little has been accomplished in the field with respect to material characterization. Yoshikawa, E., et al., Macromolecules 1994, 27, 5471. The present invention demonstrates that fluorinating biopolymers can not only impact the secondary structure and $T_t$, but, more importantly, influence the supramolecular assemblies and mechanical properties. While these fluorinated protein polymers exist as soft gels, the observed modifications to the self-assembly and rheological properties from the incorporation of non-natural amino acids provides a precedence and an opportunity for tuning protein-based materials. This provides a novel and alternative route for tuning smart materials that rely on gel mechanics, in the case of tissue engineering applications, and thermoresponsive transition, in the case of drug delivery applications.

The foregoing detailed description of the preferred embodiments and the appended figures have been presented only for illustrative and descriptive purposes and are not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

What is claimed is:

1. A protein polymer comprising:
   a) an elastin-like peptide (ELP) domain; and
   b) a coiled-coil domain of cartilage oligomeric matrix protein (COMPcc);
   wherein at least one of the ELP and the COMPcc incorporates at least one fluorinated amino acid residue.

2. The protein polymer of claim 1, wherein the COMPcc is selected from the group consisting of SEQ ID NOS 3-14.

3. The protein polymer of claim 2, wherein at least one of the ELP and the COMPcc incorporates at least one fluorinated phenylalanine.

4. A method for facilitating solubilization and protection of small molecules for use in drug delivery, comprising the steps of:
   a) providing a protein polymer comprising an elastin-like peptide (ELP) domain and a coiled-coil domain of cartilage oligomeric matrix protein (COMPcc);
   wherein at least one of the ELP and the COMPcc incorporates at least one fluorinated amino acid residue; and
   b) binding the small molecules in the protein polymer;
   whereby the protein polymer solubilizes and protects the small molecules from degradation.

5. The method of claim 4, wherein the COMPcc is selected from the group consisting of SEQ ID NOS 3-14.

6. The method of claim 5, further comprising incorporating at least one fluorinated phenylalanine into at least one of the ELP and COMPcc domains.

7. The method of claim 6, further comprising imaging the protein polymer via at least one of magnetic resonance spectroscopy (MRS) and magnetic resonance imaging (MRI).

8. The protein polymer of claim 3, wherein the at least one fluorinated amino acid residue is incorporated into at least one of the ELP and the COMPcc domains prior to assembly of the protein polymer.

9. The protein polymer of claim 3, wherein fluorination is achieved by residue-specific incorporation of p-fluorophenylalanine (pFF) to create at least one of pFF-ELP-COMPcc, pFF-COMPcc-ELP, and pFF-ELP-COMPcc-ELP.

10. The method of claim 6 wherein the at least one fluorinated amino acid residue is incorporated into at least one of the ELP and the COMPcc domains prior to assembly of the protein polymer.

11. The method of claim 6, wherein fluorination is achieved by residue-specific incorporation of p-fluorophenylalanine (pFF) to create at least one of pFF-ELP-COMPcc, pFF-COMPcc-ELP, and pFF-ELP-COMPcc-ELP.

* * * * *

SEQUENCE LISTING

<160> NUMBER OF SEQ ID NOS: 25

<210> SEQ ID NO 1
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Gly Ser His His His His His Gly Ser Gly Asp Leu Ala
1               5                   10                  15

Pro Gln Met Leu Arg Glu Leu Gln Glu Thr Asn Ala Ala Leu Gln Asp
            20                  25                  30

Val Arg Glu Leu Leu Arg Gln Gln Val Lys Glu Ile Thr Phe Leu Lys
        35                  40                  45

Asn Thr Val Met Glu Cys Asp Ala Cys Gly Lys Leu Asn
    50                  55                  60

<210> SEQ ID NO 2
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 2

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
                20                  25                  30

Thr Phe Leu Lys Asn Thr Val Met Glu Cys Asp Ala Cys Gly Lys Leu
            35                  40                  45

Asn

<210> SEQ ID NO 3
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
                20                  25                  30

Glu Leu Leu Arg Gln Gln Val Lys Glu Ile Thr Phe Leu Lys Asn Thr
            35                  40                  45

Val Met Glu Cys Asp Ala Cys Gly Lys Leu Asn
        50                  55

<210> SEQ ID NO 4
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
                20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
        50                  55

<210> SEQ ID NO 5
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Arg Gly Ser His His His His His His Gly Asp Leu Ala Pro Gln
1               5                   10                  15

Met Leu Arg Glu Ala Gln Glu Thr Asn Ala Ala Leu Gln Asp Val Arg
                20                  25                  30

Glu Leu Leu Arg Gln Gln Val Lys Glu Ile Thr Phe Leu Lys Asn Thr
            35                  40                  45
```

Val Met Glu Ser Asp Ala Ser Gly Lys Leu Asn
    50                  55

<210> SEQ ID NO 6
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Arg Gly Ser His His His His His Gly Asp Leu Ala Pro Gln
1               5                   10                  15

Met Leu Arg Glu Leu Gln Glu Ala Asn Ala Ala Leu Gln Asp Val Arg
            20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 7
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Gly Ser His His His His His Gly Asp Leu Ala Pro Gln
1               5                   10                  15

Met Leu Arg Glu Leu Gln Glu Thr Asn Ala Ala Ala Gln Asp Val Arg
            20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 8
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Arg Gly Ser His His His His His Gly Asp Leu Ala Pro Gln
1               5                   10                  15

Met Leu Arg Glu Leu Gln Glu Thr Asn Ala Ala Leu Gln Asp Ala Arg
            20                  25                  30

Glu Leu Leu Arg Gln Gln Val Lys Glu Ile Thr Phe Leu Lys Asn Thr
            35                  40                  45

Val Met Glu Ser Asp Ala Ser Gly Lys Leu Asn
    50                  55

<210> SEQ ID NO 9
<211> LENGTH: 59
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Ala Arg Gln Gln Val Lys Glu Ile Thr Phe Leu Lys Asn Thr
        35                  40                  45

Val Met Glu Ser Asp Ala Ser Gly Lys Leu Asn
    50                  55

<210> SEQ ID NO 10
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Ala Val Lys Glu Ile Thr Phe Leu Lys Asn Thr
        35                  40                  45

Val Met Glu Ser Asp Ala Ser Gly Lys Leu Asn
    50                  55

<210> SEQ ID NO 11
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

Glu Leu Leu Arg Gln Gln Val Lys Glu Ala Thr Phe Leu Lys Asn Thr
        35                  40                  45

Val Met Glu Ser Asp Ala Ser Gly Lys Leu Asn
    50                  55

<210> SEQ ID NO 12
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Arg Gly Ser His His His His His His Gly Asp Leu Ala Pro Gln
1               5                   10                  15

Met Leu Arg Glu Leu Gln Glu Thr Asn Ala Ala Leu Gln Asp Val Arg
            20                  25                  30

```
Glu Leu Leu Arg Gln Gln Val Lys Glu Ile Thr Phe Ala Lys Asn Thr
            35                  40                  45

Val Met Glu Ser Asp Ala Ser Gly Lys Leu Asn
 50                  55
```

<210> SEQ ID NO 13
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Arg Gly Ser His His His His His His Gly Asp Leu Ala Pro Gln
 1               5                  10                  15

Met Leu Arg Glu Leu Gln Glu Thr Asn Ala Ala Leu Gln Asp Val Arg
            20                  25                  30

Glu Leu Leu Arg Gln Gln Val Lys Glu Ile Thr Phe Leu Lys Asn Thr
            35                  40                  45

Ala Met Glu Ser Asp Ala Ser Gly Lys Leu Asn
 50                  55
```

<210> SEQ ID NO 14
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Arg Gly Ser His His His His His His Gly Asp Leu Ala Pro Gln
 1               5                  10                  15

Met Leu Arg Glu Leu Gln Glu Thr Asn Ala Ala Leu Gln Asp Val Arg
            20                  25                  30

Glu Leu Leu Arg Gln Gln Val Lys Glu Ile Thr Phe Leu Lys Asn Thr
            35                  40                  45

Val Met Glu Ala Asp Ala Ser Gly Lys Leu Asn
 50                  55
```

<210> SEQ ID NO 15
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Arg Gly Ser His His His His His His Gly Ser Lys Pro Ile Ala
 1               5                  10                  15

Ala Ser Ala Val Pro Gly Val Gly Val Pro Gly Val Gly Val Pro Gly
            20                  25                  30

Phe Gly Val Pro Gly Val Gly Val Pro Gly Val Gly Val Pro Gly Val
            35                  40                  45

Gly Val Pro Gly Val Gly Val Pro Gly Phe Gly Val Pro Gly Val Gly
            50                  55                  60

Val Pro Gly Val Gly Val Pro Gly Val Gly Val Pro Gly Val Gly Val
 65                  70                  75                  80

Pro Gly Phe Gly Val Pro Gly Val Gly Val Pro Gly Val Gly Val Pro
```

```
                            85                  90                  95
Gly Val Gly Val Pro Gly Val Gly Val Pro Gly Phe Gly Val Pro Gly
                100                 105                 110
Val Gly Val Pro Gly Val Gly Val Pro Gly Val Gly Val Pro Gly Val
                115                 120                 125
Gly Val Pro Gly Phe Gly Val Pro Gly Val Gly Val Pro Gly Val Gly
                130                 135                 140
Val Pro Leu Glu Gly Ser Glu Leu Ala Ala Thr Ala Thr Ala Thr Ala
145                 150                 155                 160
Thr Ala Thr Ala Thr Ala Ala Cys Gly Asp Leu Ala Pro Gln Met Leu
                165                 170                 175
Arg Glu Leu Gln Glu Thr Asn Ala Ala Leu Gln Asp Val Arg Glu Leu
                180                 185                 190
Leu Arg Gln Gln Val Lys Glu Ile Thr Phe Leu Lys Asn Thr Val Met
                195                 200                 205
Glu Ser Asp Ala Ser Gly Leu Gln Ala Ala Thr Ala Thr Ala Thr Ala
                210                 215                 220
Thr Ala Thr Ala Thr Ala Val Asp Leu Gln Pro Ser
225                 230                 235

<210> SEQ ID NO 16
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Arg Gly Ser His His His His His His Gly Ser Ala Cys Glu Leu
1               5                   10                  15
Ala Ala Thr Ala Thr Ala Thr Ala Thr Ala Thr Ala Thr Ala Ala Cys
                20                  25                  30
Gly Asp Leu Ala Pro Gln Met Leu Arg Glu Leu Gln Glu Thr Asn Ala
                35                  40                  45
Ala Leu Gln Asp Val Arg Glu Leu Leu Arg Gln Gln Val Lys Glu Ile
            50                  55                  60
Thr Phe Leu Lys Asn Thr Val Met Glu Ser Asp Ala Ser Gly Leu Gln
65                  70                  75                  80
Ala Ala Thr Ala Thr Ala Thr Ala Thr Ala Thr Ala Thr Ala Val Asp
                85                  90                  95
Lys Pro Ile Ala Ala Ser Ala Val Pro Gly Val Gly Val Pro Gly Val
                100                 105                 110
Gly Val Pro Gly Phe Gly Val Pro Gly Val Gly Val Pro Gly Val Gly
                115                 120                 125
Val Pro Gly Val Gly Val Pro Gly Val Gly Val Pro Gly Phe Gly Val
                130                 135                 140
Pro Gly Val Gly Val Pro Gly Val Gly Val Pro Gly Val Gly Val Pro
145                 150                 155                 160
Gly Val Gly Val Pro Gly Phe Gly Val Pro Gly Val Gly Val Pro Gly
                165                 170                 175
Val Gly Val Pro Gly Val Gly Val Pro Gly Val Gly Val Pro Gly Phe
                180                 185                 190
Gly Val Pro Gly Val Gly Val Pro Gly Val Gly Val Pro Gly Val Gly
                195                 200                 205
```

Val Pro Gly Val Gly Val Pro Gly Phe Gly Val Pro Gly Val Gly Val
    210                 215                 220

Pro Gly Val Gly Val Pro Leu Glu Gly Ser Gly Thr Gly Ala Lys Leu
225                 230                 235                 240

<210> SEQ ID NO 17
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Arg Gly Ser His His His His His Gly Ser Lys Pro Ile Ala
1               5                   10                  15

Ala Ser Ala Val Pro Gly Val Gly Val Pro Gly Val Gly Val Pro Gly
            20                  25                  30

Phe Gly Val Pro Gly Val Gly Val Pro Gly Val Gly Val Pro Gly Val
        35                  40                  45

Gly Val Pro Gly Val Gly Val Pro Gly Phe Gly Val Pro Gly Val Gly
    50                  55                  60

Val Pro Gly Val Gly Val Pro Gly Val Gly Val Pro Gly Val Gly Val
65                  70                  75                  80

Pro Gly Phe Gly Val Pro Gly Val Gly Val Pro Gly Val Gly Val Pro
                85                  90                  95

Gly Val Gly Val Pro Gly Val Gly Val Pro Gly Phe Gly Val Pro Gly
            100                 105                 110

Val Gly Val Pro Gly Val Gly Val Pro Gly Val Gly Val Pro Gly Val
        115                 120                 125

Gly Val Pro Gly Phe Gly Val Pro Gly Val Gly Val Pro Gly Val Gly
    130                 135                 140

Val Pro Leu Glu Gly Ser Glu Leu Ala Ala Thr Ala Thr Ala Thr Ala
145                 150                 155                 160

Thr Ala Thr Ala Thr Ala Ala Cys Gly Asp Leu Ala Pro Gln Met Leu
                165                 170                 175

Arg Glu Leu Gln Glu Thr Asn Ala Ala Leu Gln Asp Val Arg Glu Leu
            180                 185                 190

Leu Arg Gln Gln Val Lys Glu Ile Thr Phe Leu Lys Asn Thr Val Met
        195                 200                 205

Glu Ser Asp Ala Ser Gly Leu Gln Ala Ala Thr Ala Thr Ala Thr Ala
    210                 215                 220

Thr Ala Thr Ala Thr Ala Val Asp Lys Pro Ile Ala Ala Ser Ala Val
225                 230                 235                 240

Pro Gly Val Gly Val Pro Gly Val Gly Val Pro Gly Phe Gly Val Pro
                245                 250                 255

Gly Val Gly Val Pro Gly Val Gly Val Pro Gly Val Gly Val Pro Gly
            260                 265                 270

Val Gly Val Pro Gly Phe Gly Val Pro Gly Val Gly Val Pro Gly Val
        275                 280                 285

Gly Val Pro Gly Val Gly Val Pro Gly Val Gly Val Pro Gly Phe Gly
    290                 295                 300

Val Pro Gly Val Gly Val Pro Gly Val Gly Val Pro Gly Val Gly Val
305                 310                 315                 320

Pro Gly Val Gly Val Pro Gly Phe Gly Val Pro Gly Val Gly Val Pro
                325                 330                 335

```
Gly Val Gly Val Pro Gly Val Gly Val Pro Gly Val Gly Val Pro Gly
            340                 345                 350

Phe Gly Val Pro Gly Val Gly Val Pro Gly Val Gly Val Pro Leu Glu
            355                 360                 365

Gly Ser Gly Thr Gly Ala Lys Leu Asn
            370                 375

<210> SEQ ID NO 18
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Arg Gly Ser His His His His His Gly Ser Lys Pro Ile Ala
 1               5                  10                  15

Ala Ser Ala Val Pro Gly Val Gly Val Pro Gly Val Gly Val Pro Gly
                20                  25                  30

Phe Gly Val Pro Gly Val Gly Val Pro Gly Val Gly Val Pro Leu Glu
            35                  40                  45

Gly Ser Glu Leu Ala Ala Thr Ala Thr Ala Thr Ala Thr Ala Thr Ala
        50                  55                  60

Thr Ala Ala Cys Gly Asp Leu Ala Pro Gln Met Leu Arg Glu Leu Gln
65                  70                  75                  80

Glu Thr Asn Ala Ala Leu Gln Asp Val Arg Glu Leu Leu Arg Gln Gln
                85                  90                  95

Val Lys Glu Ile Thr Phe Leu Lys Asn Thr Val Met Glu Ser Asp Ala
            100                 105                 110

Ser Gly Leu Gln Ala Ala Thr Ala Thr Ala Thr Ala Thr Ala Thr Ala
        115                 120                 125

Thr Ala Val Asp Leu Gln Pro Ser
            130                 135

<210> SEQ ID NO 19
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Arg Gly Ser His His His His His Gly Ser Ala Cys Glu Leu
 1               5                  10                  15

Ala Ala Thr Ala Thr Ala Thr Ala Thr Ala Thr Ala Thr Ala Ala Cys
                20                  25                  30

Gly Asp Leu Ala Pro Gln Met Leu Arg Glu Leu Gln Glu Thr Asn Ala
            35                  40                  45

Ala Leu Gln Asp Val Arg Glu Leu Leu Arg Gln Gln Val Lys Glu Ile
        50                  55                  60

Thr Phe Leu Lys Asn Thr Val Met Glu Ser Asp Ala Ser Gly Leu Gln
65                  70                  75                  80

Ala Ala Thr Ala Thr Ala Thr Ala Thr Ala Thr Ala Thr Ala Val Asp
                85                  90                  95

Lys Pro Ile Ala Ala Ser Ala Val Pro Gly Val Gly Val Pro Gly Val
            100                 105                 110
```

```
Gly Val Pro Gly Phe Gly Val Pro Gly Val Gly Val Pro Gly Val Gly
        115                 120                 125

Val Pro Leu Glu Gly Ser Gly Thr Gly Ala Lys Leu
    130                 135                 140

<210> SEQ ID NO 20
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Arg Gly Ser His His His His His Gly Ser Lys Pro Ile Ala
1               5                   10                  15

Ala Ser Ala Val Pro Gly Val Gly Val Pro Gly Val Gly Val Pro Gly
            20                  25                  30

Phe Gly Val Pro Gly Val Gly Val Pro Gly Val Gly Val Pro Leu Glu
        35                  40                  45

Gly Ser Glu Leu Ala Ala Thr Ala Thr Ala Thr Ala Thr Ala Thr Ala
    50                  55                  60

Thr Ala Ala Cys Gly Asp Leu Ala Pro Gln Met Leu Arg Glu Leu Gln
65                  70                  75                  80

Glu Thr Asn Ala Ala Leu Gln Asp Val Arg Glu Leu Leu Arg Gln Gln
                85                  90                  95

Val Lys Glu Ile Thr Phe Leu Lys Asn Thr Val Met Glu Ser Asp Ala
            100                 105                 110

Ser Gly Leu Gln Ala Ala Thr Ala Thr Ala Thr Ala Thr Ala Thr Ala
        115                 120                 125

Thr Ala Val Asp Lys Pro Ile Ala Ala Ser Ala Val Pro Gly Val Gly
    130                 135                 140

Val Pro Gly Val Gly Val Pro Gly Phe Gly Val Pro Gly Val Gly Val
145                 150                 155                 160

Pro Gly Val Gly Val Pro Leu Glu Gly Ser Gly Thr Gly Ala Lys Leu
                165                 170                 175

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Pro Gly Val Gly Val Pro Gly Val Gly Val Pro Gly Phe Gly Val
1               5                   10                  15
```

```
Pro Gly Val Gly Val Pro Gly Val Gly
            20              25

<210> SEQ ID NO 23
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Arg Gly Ser His His His His His His Gly Ser Ala Cys Glu Leu
1               5                   10                  15

Ala Ala Thr Ala Thr Ala Thr Ala Thr Ala Thr Ala Thr Ala Ala Cys
            20                  25                  30

Gly Asp Leu Ala Pro Gln Met Leu Arg Glu Leu Gln Glu Thr Asn Ala
        35                  40                  45

Ala Leu Gln Asp Val Arg Glu Leu Leu Arg Gln Gln Val Lys Glu Ile
    50                  55                  60

Thr Phe Leu Lys Asn Thr Val Met Glu Ser Asp Ala Ser Gly Leu Gln
65                  70                  75                  80

Ala Ala Thr Ala Thr Ala Thr Ala Thr Ala Thr Ala Thr Ala Val Asp
                85                  90                  95

Lys Pro Ile Ala Ala Ser Ala Val Pro Gly Val Gly Val Pro Gly Val
            100                 105                 110

Gly Val Pro Gly Phe Gly Val Pro Gly Val Gly Val Pro Gly Val Gly
        115                 120                 125

Val Pro Gly Val Gly Val Pro Gly Val Gly Val Pro Gly Phe Gly Val
    130                 135                 140

Pro Gly Val Gly Val Pro Gly Val Gly Val Pro Gly Val Gly Val Pro
145                 150                 155                 160

Gly Val Gly Val Pro Gly Phe Gly Val Pro Gly Val Gly Val Pro Gly
                165                 170                 175

Val Gly Val Pro Gly Val Gly Val Pro Gly Val Gly Val Pro Gly Phe
            180                 185                 190

Gly Val Pro Gly Val Gly Val Pro Gly Val Gly Val Pro Gly Val Gly
        195                 200                 205

Val Pro Gly Val Gly Val Pro Gly Phe Gly Val Pro Gly Val Gly Val
    210                 215                 220

Pro Gly Val Gly Val Pro Leu Glu Gly Ser Gly Thr Gly Ala Lys Leu
225                 230                 235                 240

Asn

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Val Pro Gly Val Gly Val Pro Gly Val Gly Val Pro Gly Phe Gly Val
1               5                   10                  15

Pro Gly Val Gly Val Pro Gly Val Gly Val Pro Gly Val Gly Val Pro
            20                  25                  30

Gly Val Gly Val Pro Gly Phe Gly Val Pro Gly Val Gly Val Pro Gly
```

```
                    35                  40                  45
Val Gly Val Pro Gly Val Gly Val Pro Gly Val Gly Val Pro Gly Phe
    50                  55                  60

Gly Val Pro Gly Val Gly Val Pro Gly Val Gly Val Pro Gly Val Gly
65                  70                  75                  80

Val Pro Gly Val Gly Val Pro Gly Phe Gly Val Pro Gly Val Gly Val
                85                  90                  95

Pro Gly Val Gly Val Pro Gly Val Gly Val Pro Gly Val Gly Val Pro
            100                 105                 110

Gly Phe Gly Val Pro Gly Val Gly Val Pro Gly Val Gly Val Pro
            115                 120                 125

<210> SEQ ID NO 25
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Leu Ala Pro Gln Met Leu Arg Glu Leu Gln Glu Thr Asn Ala Ala
1               5                   10                  15

Leu Gln Asp Val Arg Glu Leu Leu Arg Gln Gln Val Lys Glu Ile Thr
            20                  25                  30

Phe Leu Lys Asn Thr Val Met Glu Ser Asp Ala Ser Gly
            35                  40                  45
```